United States Patent [19]

Friedman et al.

[11] Patent Number: 5,691,148
[45] Date of Patent: Nov. 25, 1997

[54] PETROLEUM IMMUNOASSAY METHOD, ITS COMPONENTS AND A KIT FOR USE IN PERFORMING THE SAME

[75] Inventors: Stephen B. Friedman, Chapel Hill; Randy L. Allen, Apex, both of N.C.

[73] Assignee: ENSYS, Inc., Morrisville, N.C.

[21] Appl. No.: 328,954

[22] Filed: Oct. 24, 1994

Related U.S. Application Data

[63] Continuation of Ser. No. 984,098, Dec. 1, 1992, abandoned.
[51] Int. Cl.$^6$ .................... G01N 33/577; C07K 16/44
[52] U.S. Cl. .................... 435/7.1; 435/7.92; 530/388.9; 530/389.8
[58] Field of Search ................ 530/388.9, 389.8; 435/240.27, 7.1, 7.92, 29

[56] References Cited

U.S. PATENT DOCUMENTS

| | | |
|---|---|---|
| 4,480,041 | 10/1984 | Myles et al. |
| 4,483,921 | 11/1984 | Cole |
| 4,708,933 | 11/1987 | Huang et al. |
| 5,015,586 | 5/1991 | Severn et al. |
| 5,028,535 | 7/1991 | Buechler et al. |
| 5,051,184 | 9/1991 | Taylor |

FOREIGN PATENT DOCUMENTS 8809798  12/1988  WIPO

OTHER PUBLICATIONS

Petroleum Contaminated Soils, vol. 2, Chapter 10, pp. 97–109, Thomas L. Potter, "Analysis of Petroleum Contaminated Soil and Water: An Overview".

Petroleum Contaminated Soils, vol. 2, Chapter 11, pp. 111–117, Lynne M. Preslo, et al., "Field–Screening Techniques: Quick and Effective Tools for Optimizing Hazardous Waste Site Investigations".

Petroleum Contaminated Soils, vol. 2, Chapter 12, pp. 119–136, John Fitzgerald, "Onsite Analytical Screening of Gasoline Contaminated Media Using a Jar Headspace Procedure".

Petroleum Contaminated Soils, vol. 3, Chapter 9, pp. 93–109, S.A. Denahan, et al., "Relationships Between Chemical Screening Methodologies for Petroleum Contaminated Soils: Theory and Practice".

Cancer, vol. 49, No. 10, May 15, 1982, pp. 1953–1957, General Motors Cancer Research Foundation Awards, Cesar Milstein, "Monoclonal Antibodies".

J. Agric. Food. Chem., vol. 37, 1989, pp. 1183–1187, F. Jung, et al., "Development of a Sensitive Enzyme–Linked Immunosorbent Assay for the Fungicide Fenpropimorph".

J. Agric. Food Chem., vol. 37, 1989, pp. 958–964, Robert O. Harrison, et al., "Development of a Monoclonal Antibody Based Enzyme Immunoassay Method for Analysis of Maleic Hydrazide".

Toxicology and Applied Pharmacology, vol. 50, 1979, pp. 147–155, Michael I. Luster, et al., "Production and Characterization of Antisera Specific for Chlorinated Biphenyl Species: Initiation of a Radioimmunoassay for Aroclors".

Toxicology and Applied Pharmacology, vol. 50, 1979, pp. 137–146, Phillip W. Albro, et al., "A Radioimmunoassay for Chlorinated Dibenzo–p–Dioxins".

J. Agric. Food Chem., vol. 36, 1988, pp. 863–870, Shirley J. Gee, et al., "Development of an Enzyme–Linked Immunosorbent Assay for the Analysis of the Theiocarbamate Herbicide Molinate".

(List continued on next page.)

*Primary Examiner*—Ponnathapura Achutamurthy
*Attorney, Agent, or Firm*—Oblon, Spivak, McClelland, Maier & Neustadt, P.C.

[57] ABSTRACT

An immunoassay method that integrates a sample processing component that enables the testing of a variety of environmental matrixes and the components for performing the method, wherein the immunoassay utilizes a monoclonal anti-petroleum antibody to detect the presence or absence of petroleum based contamination in a sample when tested in a field or laboratory location.

16 Claims, 3 Drawing Sheets

OTHER PUBLICATIONS

Environmental Toxicology and Chemistry, vol. 7, pp. 859–870, 1988, Environmental Chemistry, "Improvement and Application of an Immunoassay for Screening Environmental Samples for Dioxin Contamination".

Methods in Enzymology, vol. 70, 1980, pp. 104–142, B.A.L. Hurn, et al., "Production of Reagent Antibodies".

Immunofluorescence and Related Staining Techniques, 1978, pp. 215–224, M. Barbara Wilson, et al., "Recent Developments in the Periodate Method of Conjugating Horseradish Peroxidase (HRPO) to Antibodies".

Immunochemical Methods for Environmental Analysis, 1990, pp. 58–64, Chapter 7, J.M. Van Emon, "Immunoassay Methods—EPA Evaluations".

Immunochemical Methods for Environmental Analysis, 1990, pp. 21–26, Chapter 3, S. Krogsrud, et al., "Monoclonal Antibody Technology Program".

Immunochemical Methods for Environmental Analysis, 1990, pp. 1–12, Chapter 1, H. Van Vunakis, "Antibodies—Analytical Tools to Study Environmentally Important Compounds".

Immunoassays for Trace Chemical Analysis, 1991, pp. 78–85, Chapter 7, J.R. Fleeker, et al., "Reliability of Commercial Enzyme Immunoassay in Detection of Atrazine in Water".

Immunoassay for Trace Chemical Analysis, 1991, pp. 28–39, Chapter 3, J.H. Rittenburg, et al., "Rapid On–Site Immunoassay Systems—Agricultural and Environmental Applications".

Immunoassays for Trace Chemical Analysis, 1991, pp. 2–13, Chapter 1, M. Vanderlaan, et al., "Immunochemical Techniques in Trace Residue Analysis".

Eva Engvall, Ph.D., "History and Future Outlook of Enzyme Immunoassay", pp. 1–3.

T.T. Ngo, "Enzyme Mediated Immunoassay: An Overview", pp. 3–32.

William D. Odell, Chapter 1, "Introduction and General Principles", pp. 1–13.

Leaking Underground Fuel Tank Field Manual (LUFT): Guidelines for Site Assessment, Cleanup, and Underground Storage Tank Closure, May 1988, pp. i–ix, 1–121.

The Journal of Histochemistry and Cytochemistry, vol. 22, No. 12, pp. 1084–1091, 1974, P.K. Nakane, et al., "Peroxidase–Labeled Antibody—A New Method of Conjugation".

Peptides from Mixed Carbonic–Carboxylic Acid Anhydrides, vol. 74, Feb. 5, 1952, pp. 676–678, J.R. Vaughan, Jr., et al., "The Preparation of Peptides Using Mixed Carbonic–Carboxylic Aicd Anhydrides".

Bull. Environ. Contam. Toxicol., vol. 45, 1990, pp. 120–124, T.C. Blewett, et al., "Field Leaf–Test Kit for Rapid Determination of Dislodgeable Foliar Residues of Organophosphate and N–Methyl Carbamate Insecticides".

Analytical Chemistry, vol. 62, No. 18, Sep. 15, 1990, pp. 2043–2048, E.M. Thurman, et al., "Enzyme–Linked Immunosorbent Assay Compared with Gas Chromatography/Mass Spectrometry for the Determination of Triazine Herbicides in Water".

Pestic. Sci., 1989, pp. 303–317, Use of Immunochemical Techniques for Pesticide Analysis, F. Jung, et al., "Pesticides".

Bulletin of Environmental Contamination and Toxicology, vol. 46, 1991, pp. 30–36, K.S. Goh, et al., "Enzyme Immunoassay for the Determination of Atrazine Residues in Soil".

Bulletin of Environmental Contamination and Toxicology, vol. 40, 1988, pp. 647–654, R.J. Bushway, et al., "Determination of Atrazine Residues in Water and Soil by Enzyme Immunoassay".

Toxicology, vol. 45, 1987, pp. 229–243, L.H. Stanker, et al., "Monoclonal Antibodies for Dioxin: Antibody Characerization and Assay Development".

Reprinted from Environmental Lab Magazine, On Site News, A. Scallen, et al., "Field Analysis Using Rapid Immunoassay Screens", 2 pages.

Pollution Engineering, Mar. 15, 1992, pp. 36–38, K.R. Carter, Ph.d., "On–Site Screening Speeds Sample Analysis".

Reprinted from American Environmental Laboratory, 1992, 2 pages, K.R. Carter, "Immunoassay Technology for On–Site Testing".

Reprinted from Hazmat World, Dec. 1991, 4 pages, K.A. Roy, "Scientific Swapping—Onsite Analytical Technology Uses Medical Technology to Detect Organic Content".

Journal of Soil Contamination, vol. 1, No. 3, 1992, pp. 227–237, R.L. Allen, et al., "A Rapid and Sensitive Immunoassay for the Detection of Gasoline and Diesel Fuel in Contaminated Soil".

Abstracts of the Sixth Annual Conference, Aug. 1992, "Hydrocarbon Contaminated Soils: Analysis, Fate, Environmental & Public Health Effects, Remediation, and Regulation", R.L. Allen, et al., Development of a Monoclonal Antibody Immunoassay for the Detection of Gasoline and Diesel Fuel in the Environment, 2 pages.

Submitted for publication in J. Air and Waste Management Assoc., May 27, 1992, pp. 1–21, J.P. Mapes, et al., "Petro RISc Soil—An Immunoassay for the Rapid, On–Site Screening of Gasoline and Diesel Fuel in Contaminated Soil".

Contaminated Soils, Diesel Fuel Contamination, pp. 37–46, Chapter 3, R.L. Allen, et al., "Development of a Monoclonal Antibody Immunoassay for the Detection of Gasoline and Diesel Fuel in the Environment".

PCT International Search Report No. PCT/US93/11410, dated Feb. 14, 1994.

Journal of Soil Contamination, vol. 1, No. 3, issued Mar. 1992, R.L. Allen et al., "A rapid and sensitive immunoassay for the detection of gasoline and diesel fuel in contaminated soil", pp. 227–237, see entire document.

Hydrocarbon Contaminated Soils: Abstracts of the sixth annual congress, issued Aug. 1992, R. L. Allen et al., "Development of a monoclonal antibody immunoassay for the detection of gasoline and diesel fuel in the environment", p. 2, see entire document.

FIG. 3

PETROLEUM IMMUNOASSAY METHOD, ITS COMPONENTS AND A KIT FOR USE IN PERFORMING THE SAME

This application is a Continuation of application Ser. No. 07/984,098, filed on Dec. 1, 1992, now abandoned.

BACKGROUND OF THE INVENTION

1. Field of the Invention

The present invention relates to methods, compositions and kits for performing petroleum immunoassays.

2. Discussion of the Background

Testing is an essential, and integral, component of all environmental protection and restoration activities. It is the rate limiting element that influences the time, cost, and overall efficiency of project management.

The management of toxic waste sites usually involves a progression through the stages of identification, characterization, remediation and monitoring, with testing being performed during each phase. Reference laboratory methods can effectively identify and quantify unknown compounds in a sample, but become relatively inefficient when used to rapidly locate contamination (i.e., mapping), and assist in remediation and monitoring activities. The complexity of laboratory protocols, and the proximity of the labs to the test site, delays the availability of information and increases the cost of data. The ultimate cost is in the time required by the field crews. Effective field screening methods can increase the efficiency of the clean-up process by providing an on-site, high-throughput, and cost-effective way to locate contamination and manage its remediation.

The Environmental Protection Agency (EPA) has long promoted and supported the concept of screening methods to supplement laboratory analysis and increase overall efficiency. The need for more effective methods has been recognized in the Superfund Amendments and Reauthorization Act of 1986 which specifies the development and evaluation of alternative time and cost-saving methods that will assist in the eventual remediation of the nations Superfund sites.

Effective field screening methods can increase the efficiency of site management and improve overall data quality when used to supplement the services of regional laboratories. The development of these methods, however, requires a technology that will be compatible with numerous compounds and matrixes and yet be simple, effective and rugged enough to be incorporated into a protocol for use in the field.

Screening methods need to provide fast, simple, cost-effective and reliable information when operated under field conditions. The reagents and equipment should be portable and stable at ambient conditions, and the claims relating to performance should accurately reflect anticipated field use. The methods should be able to rapidly provide an ample quantity of data, and the protocol should be simple to perform and safe to use. Performance characteristics relative to sensitivity, freedom from matrix interferences and cross-reacting compounds, and correlation to an acceptable reference method should be carefully evaluated. Developers must maintain high, and consistent, quality standards relative to the consistency of their manufacturing protocols, the adequacy of in-process and pre-release quality control methods, and the reliability of their product claims. A necessary characteristic of particular significance for screening methods, is that they exhibit a very low frequency of false negative results.

Screening methods detect contamination at specified concentrations. The concentration may relate to a hazardous threshold, a clean-up target, or a process-control parameter. The potential implications of false negative data far outweigh those of false positive results. The consequence of a false positive, while a costly problem that needs to be minimized, results in additional testing or treatment. False negative data, however, provides an erroneous perception of a clean site, and may have serious environmental and legal consequences. Safeguards that minimize the incidence of false negative results are imperative. Appropriate control over the frequency of false positive data needs to be established and maintained.

The field of immunochemistry, and the development of immunoassay technology, has been evolving since the late 19th century. However, the majority of these methods have been developed for use by the medical community. These methods have achieved a reputation for reliability and cost-effectiveness. Literally hundreds of immunoassays have been developed for such applications as drug testing, Therapeutic Drug Monitoring (e.g. digitalis derivatives, anti-asthma formulations, anti-epileptic regents, antibiotics), pregnancy testing, hormone testing (e.g., thyroxine, thyroid stimulating hormone), tests for pathological markers (e.g. lactic dehydrogenase isozymes, creatine kinase isozymes), tests for acute phase proteins (e.g., carcinoembryonic antigen, alpha fetoprotein) and tests for tumor marker proteins.

Environmental applications have been explored for the better part of a decade and a number of immunoassay methods have been developed. Most have been used for the detection of herbicides and pesticides in aqueous matrixes. The application of immunoassay technology to the testing of solid waste, complex matrixes, and highly lipophilic compounds, has provided unique challenges for the chemist. The feasibility of developing such methods, however, has been demonstrated with immunoassays for single compounds such as Dioxin (see, for example, Vanderlaan et al, *Environmental Toxicology and Chemistry*, 7:859–870, 1988; and Stanker et al, *Toxicology*, 45:229–243, 1987).

The history of immunoassay technology can be traced to 1900 when Karl Landsteiner described the A, B and Zero (0) blood types after observing the agglutination reaction (i.e., aggregation) that resulted when he mixed the erythrocytes and serum for several of his co-workers on a slide. His observation became the basis for present day blood typing methods. Landsteiner remained a dominant figure in immunology for the next 40 years performing numerous experiments that demonstrated the extraordinary specificity of the antibody binding reaction. He introduced the term "hapten" to define compounds that are unable to directly stimulate antibody production when injected into an animal, but are capable of binding to an antibody if they are produced by an alternate means. Most environmental chemicals are haptens, and although potentially toxic, will not stimulate the immune system to respond.

For 50 years following Landsteiner's discovery, immunoassay technology continued to rely upon the binding and cross-linking ability of an antibody to cause agglutination, cell lysis, and protein flocculation reactions. These methods were relatively insensitive when compared to the immunoassay methods of today, and better suited to the analysis of larger compounds and organisms (e.g. bacteria, proteins). A major advance occurred in the 1950's when Drs. Berson and Yalow, while investigating the metabolism of radiolabelled insulin administered to diabetic patients, observed the production of anti-insulin antibodies in the serum of these patients (see *Principles of Competitive Protein Binding Assays*, Second Ed., Odell, W. D. and Franchismont, P. (Eds.); Wiley and Sons, New York). They described a radioimmunoassay (RIA) method in 1959 that used antiinsulin antibody molecules and radio-labelled insulin in a highly sensitive procedure to quantify insulin levels in the serum. The RIA method used a competitive antibody binding reaction, where radio-labelled insulin and sample insulin compete for a limited number of antibody binding sites. In 1977, Rosalyn Yalow was awarded the Nobel Prize in Medicine for her work on the development of the radioimmunoassay method for peptide hormones (see *Basic Clinical Immunology*, 7th Ed. Stites, D.P. and Ten, A.I. editors; Appleton and Lange, Connecticut, 1991). RIA rapidly became a universally accepted method that demonstrated exceptional specificity, sensitivity, and simplicity.

A simpler, safer, and more convenient immunoassay was reported in 1971, when two independent research teams, Engvall and Perlmann, and Van Weeman and Shuurs, simultaneously disclosed a competitive immunoassay method that used an enzyme-labelled conjugate instead of a radio-labelled-conjugate to produce a test that generated a visible end-point signal (see En all et al, *Immunochem*.8:871–874, 1971 and Van Weeman et al, *FEBS Letters*, 15:232–236, 1971). The new ELISA (i.e., enzyme linked immunosorbent assay) method eliminated the problems associated with the safety, disposal and detection of radioactive reagents. The method offered long term stability, the opportunity to generate quantifiable data using instruments commonly available in most laboratories, and a mechanism to develop separation-free (homogeneous) procedures and simple qualitative screening tests.

Current immunoassay technology benefits from the diversity of detection systems developed that use enzyme-catalyzed chromogenic reactions, radionuclides, chemiluminescence, fluorescence, fluorescence polarization and a variety of potentiometric and optical biosensor techniques. Improvements in the sensitivity achieved has necessitated the generation of new descriptive nomenclature for methods that can now detect "zeptomolar" ($10^{-21}$, 600 molecules) concentrations.

Immunoassay methods combine the specific binding characteristics of an antibody molecule with a read-out system that is used to detect and quantify compounds. Antibodies are binding proteins that are produced by the immune system of vertebrates in response to substances that are perceived to be foreign.

The physiological role of antibody, or immunoglobulin, molecules is to bind, and thereby label for destruction, the perceived foreign substance. Antibody molecules are synthesized by a subset of lymphocytes, termed B lymphocytes, that become activated to produce antibody after exposure to substances having prerequisite size, complexity and "foreignness" to the host organism. Antibodies are large, polymeric proteins (i.e. $\geq 1.5 \times 10^5$ d), that can be classified into sub-populations on the basis of their sequence, size and number of subunits. Five major populations, or isotypes, exist carrying the designations of IgM, IgA, IgD, IgG and IgE, with immunoglobulin G (IgG) usually found in the highest concentration.

The most widely used products responsible for environmental contamination are refined petroleum products. The contamination of soil and groundwater by petroleum products during transport, storage, treatment and disposal is a frequent occurrence. In an attempt to establish the magnitude of the problem, a recent study by the EPA's Underground Storage Tank Program estimated that the U.S. contains approximately 1.4 million underground storage tanks and as many 400,000 of these tanks may be leaking (see Schwenndeman et al, in *Underground Storage Systems: Leak Detection and Monitoring*. Lewis Publishers, Inc., Chelsea, Mich., 1987, 16; *Federal Register*, Vol. 52, No. 74, 12664 (1987)).

Currently, reference methods for detecting contamination at sites include analysis for benzene, toluene, xylene, ethylbenzene and petroleum hydrocarbons. These methods require laboratory analysis by GC or infrared (IR) methods and an extended period of time to obtain the results (see Potter, in *Petroleum Contaminated Soils*, eds., Calabrese et al, Vol. 2, Lewis Publishers, Chelsea, Mich., 97 (1990)). Field analysis for total petroleum hydrocarbons by hydrocarbon vapor analyzers is almost instantaneous and potentially useful. However, these instruments have shown poor correlation with laboratory-derived results due to several factors, including environmental conditions, sample aging, calibration procedures, and instrument response time (see Denahan et al, in *Petroleum Contaminated Soils*, eds., Kostecki et al, Vol. 3, Lewis Publishers, Chelsea, Mich., 93 (1990); Preslo et al, in *Petroleum Contaminated Soils*, etd., Calabrese et al, Vol. 2, Lewis Publishers, Chelsea, Mich., 111 (1990); Fitzgerald, in *Petroleum Contaminated Soils*, eds., Calabrese et al, Vol. 2, Lewis Publishers, Chelsea, Mich., 119 (1990)). Additionally, hydrocarbon vapor analyzers can not be used to detect contamination by semi-volatile hydrocarbon components (diesel fuel), because of the relatively low volatility of the hydrocarbon components *Leaking Underground Fuel Tank Field Manual*, State of California Leaking Underground Fuel Tank Task Force, Sacramento, Calif. (1988). While the hydrocarbon vapor analyzers can be useful because they provide rapid results, they would be much more useful if they accurately reflected the amount of hydrocarbons in a soil sample and detected the more persistent contamination from semi-volatile components.

Immunochemical assays are reliable when used in the screening of soil for contamination by refined petroleum fuel products. Immunochemical assays have been used commercially for the rapid analysis of a variety of compounds (see Ngo, in *Enzyme-Mediated Immunoassay*, eds., Debtor et al, Plenum Press: New York, 3 (1985); Odell, in *Principles of Competitive Protein-binding Assays*; eds., Odell et al, J. Wiley & Sons, New York, 1 (1971); *Quantitative Enzyme Immunoassay*; Blackwell Scientifid, Oxford (1978); Engvall., in *Enzyme Immunoassay*, eds., E. Ishikawa et al, Igaku-Shoin, New York, 1 (1981); Jaklitsch, in *Enzyme-Mediated Immunoassay*, eds., Debtor et al, Plenum Press, New York, 33 (1985)), and have been developed to detect a number of different compounds of environmental concern (see *Immunochemical Methods for Environmental Analysis*; ACS Symposium Series 442; Amer. Chem. Soc., Washington, DC (1990); Mapes et al, *Bull. Environ. Contam. Toxicol.* 49, in press (1992); *Immunoassays for Trace Chemical Analysis*; ACS Symposium Series 451, Amer. Chem. Soc., Washington, DC (1990); Harrison et al, in *Biotechnology for Crop Production*, Hedin et al, eds., ACS Symposium Series 379; Amer. Chem. Soc.: Washington, DC, 316 (1988); Hammock et al, in *Recent Advances in Pesticide Analytical Methodology*; Harvey et al, eds., ACS Symposium Series 136; Amer. Chem. Soc.: Washington, DC, 321 (1980); Van Emon et al, in *Analytical Methods for Pesticide and Plant Growth Regulators* Vol. XXII, 217 (1989); Albro et al, *Tox & Appl. Pharm.* 50:137 (1979); Blewett et al, *Bull Environ. Contam. Toxicol.* 45:120 (1990);

Bushway et al, *Bull Environ. Contam. Toxicol.* 40:647 (1988); Fleeker et al, in *Immunoassays for Monitoring Human Exposure to Toxic Chemicals*; Vanderlaan et al, eds., ACS Symposium Series #451 (1991); Gee et al, *J. Agric. Food Chem.* 36:863 (1988); Goh et al, *Bull. Environ. Contam. Toxicol.* 46:30 (1991); Harrison et al, Agric. Food Chem. 37:958 (1989); Jung et al, *J. Agric. Food Chem.* 37: 1183 ( 1989 ); Jung et al *Pesticide Science* 26:303 (1989); Thurman et al, *Anal. Chem.* 62:2043 (1990)). Additionally, because the composition of petroleum products varies from product to product, from manufacturer to manufacturer in the same product and even from lot to lot within the same product from a single manufacture, test development is difficult.

Thus, an immunoassay method is needed which will provide reliable accurate and fast results in the field for a wide range of petroleum based contaminants, regardless of manufacturer or exact composition. Such an assay would increase the efficiency of environmental site management activities such as characterization (mapping), remediation monitoring, and regulatory compliance.

SUMMARY OF THE INVENTION

Accordingly, one object of the present invention is to provide a petroleum-based fuel immunoassay method which is field compatible, fast and accurate.

A further object of the present invention is to provide a petroleum-based fuel immunoassay method which gives minimal false negative results.

Another object of the present invention is to provide a petroleum-based fuel immunoassay method which detects petroleum-based fuel contamination derived from a wide variety of unknown sources equivalently, where such method is independent of the detection of a single component in the petroleum-based fuel contaminant, since concentrations of single components vary between petroleum-based fuel products.

Another object of the present invention is to provide a petroleum-based fuel immunoassay which is simple to perform and easy to interpret in a field or laboratory setting by operators inexperienced in the art.

Another object of the present invention is to provide an anti-petroleum-based fuel monoclonal (MAb) antibody which is useful in the above-mentioned petroleum immunoassay.

Another object of the present invention is to provide an anti-petroleum-based fuel monoclonal antibody with specific reactivity towards a characteristic plurality of compounds found in petroleum-based fuels, namely unsubstituted bi- and tri-cyclic aromatic hydrocarbons, at least some of the mono- or poly-$C_{1-2}$-alkylated derivatives of monocyclic aromatic hydrocarbons, and certain aliphatic compounds found in petroleum-based fuels.

Another object of the present invention is to provide a reagent (e.g., an enzyme conjugate reagent) for use with the monoclonal antibody in competitive binding type immunoassays.

Another object of the present invention is to provide immunogens which elicit an anti-petroleum-based fuel monoclonal antibody response.

Another object of the present invention is to provide a kit for performing a petroleum-based fuel immunoassay.

These and other objects of the present invention, which will become apparent from a reading of the description of the invention given hereinbelow, have been found by the inventors to be satisfied by their discovery of a monoclonal antibody which recognizes a characteristic plurality of compounds common to a variety of petroleum-based fuel products, and to the inventors' discovery of immunogens which can be used to generate such a monoclonal antibody.

Petroleum-based fuel products, of different sources, differ from each other with regard to their particular chemical composition. However, they all have in common a characteristic plurality of compounds, although the relative amounts of each individual compound in this plurality may vary from one petroleum-based fuel product to another. The antibody of the present invention recognizes this characteristic plurality of compounds common to chemically diverse petroleum products with relative equivalency, and can therefore be used to detect the presence of petroleum-based fuel (contamination) in a sample since the concentration of the pool of characteristic compounds detected by the antibody is relatively constant in chemically disparate petroleum-based fuel products.

The present invention accordingly provides, among its varied embodiments, both an antibody and a test kit which incorporates the antibody. The kit is useful to detect the presence of petroleum-based fuel (contamination) in a sample because the antibody exhibits approximately equivalent detection of petroleum fuel contamination, regardless of product, manufacturer, or diversity of chemical composition, and thereby provides an easy-to-use and highly reliable kit for environmental testing applications.

BRIEF DESCRIPTION OF THE FIGURES

A more complete appreciation of the present invention and many of the attendant advantages thereof will be readily obtained as the same becomes better understood by reference to the following detailed description when considered in connection with the accompanying figures, wherein.

DETAILED DESCRIPTION OF THE PREFERRED EMBODIMENTS

In one embodiment, the present invention provides an immunoassay for determining the presence of petroleum-based fuel (contamination) in a sample (suspected to contain petroleum-based fuel). The immunoassay comprises:

(i) contacting a monoclonal antibody with specific reactivity towards the characteristic plurality of compounds found in petroleum-based fuels, with a mixture of the sample and a reagent which is cross reactive with the monoclonal antibody, to form an assay mixture;

(ii) incubating the assay mixture to allow competitive binding to the antibody between at least one member of the characteristic plurality of compounds from the petroleum-based fuel, if present, in the sample and the reagent to form a monoclonal antibody complex; and (iii) detecting the extent of binding of the reagent to the monoclonal antibody and correlating the amount of bound reagent to the amount of petroleum-based fuel in the sample.

In another embodiment, the invention provides an immunoassay kit which comprises three basic components: (1) a monoclonal antibody with specific reactivity towards a characteristic plurality of compounds in petroleum-based fuel products, (2) a reagent cross reactive with the monoclonal antibody and susceptible to detection, and optionally (3) a signal-generating reagent.

To induce, in a vertebrate host, the formation of the present monoclonal antibodies that can be used to detect the characteristic plurality of petroleum-based fuel compounds, an immunogen is used which contains a derivative moiety which mimics the structural features of the characteristic plurality of compounds found in petroleum-based products. The immunogen is synthesized, by standard methods, by coupling a derivative moiety to an immunologic carrier molecule.

Examples of suitable methods include coupling carbohydrates by periodate oxidation and coupling to amines by mixed anhydride chemistry (see Huru et al in *Methods in Enzymology* (Colowick and Kaplan, Eds.) 70:104–142, Academic Press, N.Y. (1980); Wilson et al in *Immunofluorescence and Related Staining Techniques* (Knapp et al, Eds.) pp. 215–224, Elsevier/North Holland, Amsterdam (1978); and Nakane et al, *J. Histochem. Cytochem.* 22:1084 (1974) for periodate methods; and see Erlanger et al, *J. Biol. Chem.* 228:713 (1957); Greenstein et al in *Chemistry of the Amino Acids*, Vol. 2, Wiley, N.Y. (1961); and Vaughan et al, *J. Am. Chem. Soc.* 74:676 (1952) for mixed anhydride methods.

Known immunological carrier moieties can be used, including albumin (e.g., bovine serum albumin), thyroglobulin (e.g., bovine thyroglobulin), hemocyanin (e.g., keyhole limpet hemocyanin), polyamino acids and other molecules having a minimum size, complexity, and foreignness to the host animal. Carriers are usually of the class of proteins, polypeptides or peptides having a molecular weight of at least 1,000 daltons and preferably >10,000 daltons. Carrier molecules may have a reactive group(s) available for covalent conjugation of the derivative. R-groups (e.g., COOH, $NH_2$) of amino acids or sugar moieties of glycoproteins are often used for this purpose in the synthesis of immunogens.

Preferably, the immunogen is a compound of the formula wherein
$R^1$ to $R^5$ are each independently H, $CH_3$ or $CH_2CH_3$;
X and Y are each, independently or a single bond wherein $R^6$ is selected from the group consisting of H, $C_1$–$C_2$ alkyls, and linear, branched and cyclic $C_3$–$C_6$ alkyls;
n is 0 or an integer from 1 to 4
where Z is an immunologic carrier molecule and the rest of the molecule is the derivative moeity of the immunogen.

Preferably one or two of $R^1$ to $R^5$ is methyl. A most preferred immunogen is Small environmental chemicals, such as toluene and xylene, by themselves are too small to stimulate an immune response and elicit an antibody response. To elicit an antibody response, derivatives of small molecules, such as xylene and toluene, are attached through a chemical bridge to a much larger "carrier" molecule prior to immunization. According to the invention, the small molecules and accompanying bridge structures of the derivative are designed so that they mimic immunologically at least one common feature present in the defined molecular pool of interest. A number of modifications to the bridge structure (X—($CH_2$)$_n$—Y) are possible and produce similar results. Any vertebrate is a suitable host for the immunization procedure, such as mice, rats, dogs, pigs and other domestic animals, with mice being preferred.

The immunoassay method of the present invention uses a hybridoma-derived, monoclonal antibody. The monoclonal antibody is selected using a multi-parameter screening process. A reactive panel profiling system is developed to identify appropriate cell lines and monoclonal antibodies on the basis of sensitivity, petroleum product recognition characteristics, and freedom of interference from confirmed negative soil samples or cross-reacting compounds. The monoclonal antibody binds selectively to a defined pool of molecules present in a variety of petroleum products (e.g. gasoline, diesel, kerosene, aviation and jet fuels). The antibody allows the method to rapidly detect petroleum product contamination, regardless of manufacturer or octane level, at, or above, a concentration of 10 ppm in soil at a >95% confidence level, with lower concentrations detectable at lower confidence levels. The antibody operates through the selective recognition of specific monocyclic aromatic, polycyclic aromatic compounds and alkylated derivatives thereof, and aliphatic compounds.

The reagent of the present invention, which in a preferred embodiment is an enzyme conjugate reagent, is cross reactive with the monoclonal antibody and capable of providing a detectable signal, either alone or in combination with a co-reagent. Preferably, the enzyme-conjugate reagent comprises a compound of formula wherein
$R^1$ to $R^5$ are each independently H, $CH_3$ or $CH_2CH_3$;

X and Y are each, independently or a single bond wherein $R^6$ is selected from the group consisting of H, $C_1$-$C_2$ alkyls, and linear, branched and cyclic $C_3$-$C_6$ alkyls; and n is 0 or an integer from 1 to 4.

A preferred enzyme (reporter moeity) for use in the enzyme-conjugate reagent of the present invention includes an enzyme selected from the group consisting of horseradish peroxidase, alkaline phosphatase, and β-galactosidase, with horseradish peroxidase being most preferred.

A most preferred enzyme conjugate reagent is 2-(3,5-xylyl)-acetic acid, N-(2-ethylamino)-amide coupled to horseradish peroxidase.

The enzyme conjugate is prepared using conventional methods. Illustratively, numerous functional groups on enzyme molecules (e.g. amino, sulfhydryl, carboxyl, carboxamide, tyrosyl, sugars) offer convenient points for the attachment for the ligands. As is known, enzymes enhance the sensitivity of the method by the catalytic amplification of the detection signal. A single molecule of the enzymes commonly used in immunoassay methods will convert approximately $10^6$ molecules of a substrate into a product within one minute at ambient temperatures. Catalysis is a function of the conformation at the enzyme's catalytic site, and it is this conformation, and the alignment of certain amino acid residues at spatially significant positions, that influences its rate and selectivity. The catalytic site is maintained by non-covalent (i.e. hydrophobic, hydrogen bonding, ionic and Van der Waals interactions) and covalent (i.e. disulfide) forces, and can be influenced by temperature, the binding of ions, chaotropic agents, detergents, lipids, etc.. It is therefore important to normalize and correct for anticipated variations in the reaction environment.

The enzyme conjugate of the present invention must be cross-reactive with the anti-petroleum antibody of the present invention and capable of inducing a detectable change in the sample by reaction with a signal producing substrate or reagent used in the immunoassay.

The immunoassay-based system of the present invention uses a signal producing reagent which, upon reaction with the bound enzyme conjugate/antibody complex after incubation, provides a detectable signal indicating the presence or absence of petroleum based contamination in the sample being tested. Suitable signal producing reagents include a hydrogen peroxide/tetramethyl benzidine pair, or a phenylene diamino, in combination with an enzyme conjugate reagent containing horseradish peroxidase, o-nitro-β-D-galactopyranoside (ONGP) in combination with an enzyme conjugate reagent containing β-galactosidase, and o-nitrophenylphosphate in combination with an enzyme conjugate reagent containing alkaline phosphatase. The method of the present invention preferably uses the combination of a hydrogen peroxide ($H_2O_2$) substrate solution with a tetramethylbenzidine (TMB) chromogen, with the combination producing a blue chromophore upon oxidation by $H_2O_2$, of TMB.

An important characteristic of the immunoassay of the present invention, as well as with any field screening method, is the minimization of false negative results without producing excessive false positive data. Statistically, therefore, the standard concentration should not be set at the concentration of interest, but below it. Setting the standard concentration to coincide with the regulatory concentration would result in a 50% false negative incidence. To minimize this effect, standards used in the immunoassay of the present invention should be offset in concentration to produce a >95% confidence level of detecting contamination at, or above, the desired level. For example, to obtain a method which gives results having a >95% confidence level for detection of gasoline at 10 ppm, a 7 ppm standard could be used. The standard is set below the target level. The actual concentration of standard used is a function of the binding characteristics of the assay and the overall precision of the method.

Immunoassay methods have conventionally been used to test liquid matrixes such as blood, urine, and water. This method is designed to test also solid matrices. However, the testing of solid matrices requires that the issues of sample collection, dispersion, extraction and clarification be addressed and integrated with the immunoassay component. While the assay of the present invention may be performed on samples of a wide range of qualities, a reproducible, particulate-free, leachate is preferred for optimum results. The extraction and recovery of a compound from soil requires the selection of an appropriate solvent system, adequate sample dispersion, sufficient time for partitioning, non-invasive clarification and compatibility with the subsequent immunochemistry. However, current sample processing by analytical methods is slow and expensive.

One suitable method for sample preparation involves the gravimetric collection of a 10 g sample using a small battery-operated balance. The sample is then transferred into a dispersion vial containing methanol and conventional dispersing pellets, and is subjected to a one minute manual agitation for adequate dispersion and partitioning of the ligand into the solvent. Filtration of the sample suspension to produce a particulate-free leachate can be accomplished using a fingertip-operated filter unit fitted with non-adsorbing filters. The clarified leachate is then ready for testing with the immunoassay of the present invention following dilution or otherwise removal of the solvent. Solvent-resistant antibody reagents could be used to eliminate or limit the need for the solvent or dilution step.

Buffers, detergents (e.g. Tweens, Tritons, etc.) or solvents, used alone, or in combination, have proven to be effective for extraction. Analytical methods for the analysis of solid waste rely upon gravimetrically collected samples, and results are reported in gravimetric units. Volumetric sampling for solid waste should preferably be avoided because of the potential bias that may be caused by the specific gravity of the sample.

The present imunoassay method permits the simultaneous testing of soil samples for contamination at multiple concentrations to facilitate the construction of contamination contour profiles. The method is preferably for screening purposes and several safeguards have been incorporated to minimize the incidence of false negative results.

The basic characteristics of specificity and equivalent detection of the assay of the present invention are a result of the monoclonal antibody (MAb) and the reagent. The assay provides equal recognition of different petroleum-based products (e.g. gasoline, diesel, kerosene, aviation and jet fuel), equal recognition of gasolines from different manufacturers having different chemical compositions and with different octane ratings, low cross-reactivity with unrelated compounds and is not significantly affected by normally found constituents of negative soil extracts, such as humic acid and fulvic acid.

Conventional hybridoma techniques are employed to prepare the anti-petroleum monoclonal antibody (MAb) for the assay of the present invention, by the use of the immunogen reagent of the present invention. The method for producing MAbs is extremely powerful and allows for the preparation of a defined and reproducible Ab reagent with a unique, chosen specificity (see Milstein, *Cancer*, 49:1953–1957, (1982)). The production of polyclonal antisera is much less controlled since polyclonal antisera are the product of numerous Ab populations with varying specification and sensitivity characteristics. An immunoassay for petroleum products has been marketed using polyclonal antisera, but has been shown to exhibit a number of problems, such as variability in specificity and recognition. MAbs are also homogeneous with a defined specificity, unlike polyclonal antisera which contain a mixed population of antibodies. Hybridoma cell lines provide access to an unlimited supply of MAb reagent that provides performance characteristics to the test system that will be exactly the same from lot to lot.

A unique strategy is used for antibody production. This strategy involves developing an antibody to one or more specific structural elements that are present on a defined set of compounds in petroleum products. Because of the chemical complexity of petroleum products and the tendency of the composition to vary between products and among manufacturers, the antibody is designed to recognize a defined pool of compounds. Recognition of a panel of compounds, instead of a single compound, allows the assay of the present invention to average out the concentration difference of any single component present in the different types of petroleum products. Additionally, recognition of a collection of compounds rather than a single constituent contributes significantly to the sensitivity of the assay.

Preferably the pool of compounds selected for detection by the assay are predominantly the monocyclic aromatic and polycyclic aromatic compounds and their alkylated derivatives found in petroleum-based fuels. Most preferably the compounds include the aromatic compounds xylene, toluene and ethylbenzene and the polycyclic aromatic hydrocarbon compounds (PAHs) naphthalene, methylnaphthalene, phenanthrene and acenaphthene. The immunogen of the present invention is used to immunize suitable hosts, such as mice.

Hosts responding to the immunization protocol are selected as splenocyte (or lymphoid cell) donors for hybridoma production. A culture of immune splenocytes in a defined tissue culture medium, such as HAT, with conventional modified myeloma cells, capable of providing a hybridoma, provides the fusion products s-s, s-m, and m-m (with s=splenocyte and product normally has a short lifetime and dies within days. Also, the m-m fusion product has a very short lifetime in the tissue culture medium used, lacking the metabolic components needed for protein synthesis. However the s-m fusion product (or hybridoma) survives in tissue culture and retains the Ab-producing characteristics of the splenocyte parent, and the high rate of growth and relative immortality of the myeloma cell parent. This hybridoma cell line replicates itself readily in culture producing daughter cells that provide reproducible, homogeneous, and provide a consistent supply of the monoclonal anti-petroleum antibody of the present invention.

The structure of the reagent can have a significant influence on immunoassay performance. Both the small molecule portion and the bridge structure of the derivative play an important role in antibody binding. Antibody and reagent pairs should be able to satisfy the following criteria:

Recognition and displacement by xylene or toluene in the sample

Recognition and displacement by selected monocyclic aromatic and polycyclic aromatic compounds in a sample Recognition and displacement and prerequisite sensitivity for gasoline and other petroleum-based products in a sample Low cross-reactivity to non-related compounds Approximately equal sensitivity for different types of gasoline and petroleum products Insignificant negative soil matrix effects Antibody and reagent pairs which best satisfy the above criteria are most suitable for the assay of the present invention.

The immunoassay of the present invention is performed according to the following procedure. Monoclonal anti-Petroleum antibody is immobilized in an assay vessel, or other solid support, preferably to the bottom of a polystyrene tube, at a concentration, of from 0.005 to 20 µg/tube, preferably 0.1 to 0.4 µg/tube. The concentration and affinity of the antibody for the sample molecules and reagent molecules directly influences the overall sensitivity of the final method. High, equivalent, affinity, and minimal non-specific signal generation, produces assays having superior sensitivity, with affinity binding constants, Ka, from $10^4$–$10^{12}$ L/mol, preferably $10^4$–$10^9$ L/mol.

The assay of the present invention compares a sample to be tested with a standard solution containing a compound cross-reactive with the antibody of the present invention, which is present in the standard solution in an amount sufficient to provide a 95% confidence level for detection at the desired level.

By way of example, the following describes a simultaneous test of a negative sample, a sample containing >100 ppm of gasoline, and a standard solution containing the equivalent of approximately 75 ppm of gasoline. Initially, following extraction from soil, the samples and standard are added to separate, and identical, antibody-coated test tubes. To each tube is added an equal volume of the reagent solution. The tubes are then allowed to incubate at ambient conditions for approximately ten minutes.

During the incubation period sample molecules and reagent molecules compete for the limited number of antibody binding sites that are available on the bottom of each of the tubes. The antibody concentration present is insufficient to permit the binding of all of the sample and reagent molecules simultaneously, and a situation somewhat analogous to the game of musical chairs exists, with the limited antibody binding capacity serving as the chairs in this example. The concentration of reagent immobilized in each tube after incubation is inversely proportional to the concentration of gasoline in the sample or standard. The standard in the Standard tube limits the binding of reagent, the Negative sample permits more reagent to bind (relative to the standard), and the positive sample limits the binding of the reagent (relative to the standard). At the end of the 10 minute incubation period, the tubes are washed leaving only the reagent that was retained by the immobilized antibody on the bottom of each tube.

The bound reagent/antibody complex remaining is next used to produce a detectable signal. Upon addition of a signal forming reagent, preferably a substrate/chromogen reagent, the enzyme molecules catalyze the formation of a detectable signal. The signal that is generated is directly proportional to the concentration of reagent present. A preferred substrate/chromogen reagent is $H_2O_2$ and tetramethyl-benzidine (TMB) which, when used with a preferred reagent wherein the reporter molecule is an enzyme, reacts with the enzyme portion of the reagent. $H_2O_2$ oxides TMB and generates a blue color.

Thus, the negative sample tube rapidly produces a solution that is visibly darker (i.e. greater absorbance) than the standard tube. The positive test sample produces a solution having less color (i.e. lower absorbance) than the standard tube. By comparing the signal of the sample tubes to the signal of the standard tube using a battery-operated comparative photometer, optionally included with the kit of the present invention, samples containing greater than or equal to the desired level of contamination can be detected with >95% confidence. In this competitive ELISA method the final absorbance is inversely proportional to the ligand concentration present in the test sample.

The assay method of the present invention can process multiple samples in less than 30 minutes. The method is self-contained, field-compatible and does not require refrigeration or use hazardous components. The detection level can be set at the users discretion, with 2.5 ppm as the maximum obtainable sensitivity obtainable using solid matrix samples and 30 ppb for aqueous samples.

The kit of the present invention contains five basic components: (1) a sample processing component for preparing the sample for testing by the assay method (described above), (2) at least one assay vessel, preferably a plurality, containing an amount of an immobilized anti-petroleum monoclonal antibody, equivalent amounts when a plurality of vessels is used, (3) a standard solution containing the equivalent of 5–200 ppm preferably 5–10 ppm (for soil) of a component of petroleum-based fuel in a suitable carrier, (4) a reagent which is reconstituted to form a solution containing a reagent which is cross-reactive with the monoclonal anti-petroleum antibody, in a suitable carrier, where the reagent is preferably a lyophilized enzyme-conjugate reagent, and (5) means for forming and detecting a signal indicating the presence or absence of petroleum based contamination in the sample being tested. Optionally, the kit contains one or more of the following additional components: (6) wash solutions for performing the wash step of the assay method, (7) weighing boats into which the sample is weighed using (8) a battery-operated scale, (9) one or more filters for preparing a clarified leachate sample, (10) one or more dilution vials, (11) substrate solution and (12) stop solution to halt signal formation by the signal-forming reagent. Preferably the assay is provided in a coated-tube formate in which the means for forming and detecting a signal comprises the use of a substrate/chromogen reagent which forms a detectable colored signal with the level of petroleum based contamination determined by comparison of the color developed by the test samples to the color of the kit standard. In order to eliminate temperature variations, timing errors and operator mistakes, the standard is preferably run in parallel with the samples. Therefore, any assay variations will equally affect both the standard and the samples. Using this format with the standard run in parallel, the assay has the following characteristics:

1. The sensitivity in solid samples 10 ppm for gasoline, 15 ppm for kerosene, 15 ppm for fuel oil $H_2$, 25 ppm for JP-4 (military fuel), 25 ppm for jet fuel and 15 ppm for diesel fuel.

2. The antibody is specific for both volatile and semi-volatile petroleum products.

3. Different soil matrices cause little interference in the assay.

4. The test is reproducible from lot-to-lot, day-to-day, and person-to-person.

5. The assay is operable over a temperature range of 4°–37° C., preferably 15°–37° C.

6. Storage at room temperature (up to 30° C.) is acceptable.

The immunoassay of the present invention has many advantages, including field screening compatibility, speed in obtaining a result, and a lack of false negative results. Specific characteristics had to be integrated into the method in order to achieve these advantages. The first was to minimize the incidence of false negative results. A false negative test does not detect a contaminated sample and therefore, can be potentially dangerous both to the customer and the environment. A false positive, on the other hand, might be inconvenient but not dangerous. Therefore, the immunoassay of the present invention was designed to detect positive solid matrix samples containing 10 ppm for gasoline, 15 ppm for kerosene, 15 ppm for fuel oil $H_2$, 25 ppm for JP-4 (military fuel), 25 ppm for jet fuel and 15 ppm for diesel fuel with a minimum of false negative results. This is accomplished by using a standard containing the equivalent of gasoline in soil at 6 ppm to detect 10 ppm gasoline with a 95% confidence level. Preferably, two standards are run with each assay to minimize false negative results and to provide an internal quality control parameter indicating the precision of each assay.

The immunoassay has also been simplified by making it a semiquantitative test using a standard at a single concentration. The use of one standard concentration greatly simplifies the test protocol and eliminates the data manipulation and expensive instrumentation that are normally necessary for quantitative tests. The test becomes a semiquantitative "yes/no" test that determines whether a soil sample contains greater or less than a set level of petroleum based contamination, depending on the concentration of the assay standard. The use of multiple standards at varying concentrations allows one to perform a quantitative assay by comparison to the signals produced by the samples on a concentration vs. signal plot.

The immunoassay of the present invention makes possible the rapid screening of numerous samples in the field for both volatile and semi-volatile refined petroleum products. The rapid, on-site screening of multiple samples is a significant advantage compared to the standard analytical GC or IR methods and the ability to detect semi-volatiles is a distinct advantage compared to hydrocarbon vapor analyzers. The quick screening of samples allows quick answers to important questions concerning the project, such as, has the plume of contaminated soil been located, has the area been remediated to acceptable levels, and does additional soil need to be removed?. With the immunoassay method of the present invention, personnel, time and equipment can be used more cost-effectively.

Having generally described this invention, a further understanding can be obtained by reference to certain specific examples which are provided herein for purposes of illustration only and are not intended to be limiting unless otherwise specified.

EXAMPLES

Example 1

Preparation of Assay Components Preparation of Monoclonal Antibody

Female Balb/c mice received a primary subcutaneous immunization with 50 ug of xylene derivatized to bovine serum albumin in adjuvant (MPL+TDM Emulsion, RIBI Immunochem Research, Inc., Hamilton, Mont.). Subcutaneous secondary injections (25 ug) were given at day 21, 35, and then monthly. The production of monoclonal antibodies was performed according to conventional procedures (see Milstein, *Cancer*, 49:1953–1957 (1982)). Hybridoma cultures producing monoclonal antibodies recognizing free hapten by EIA were cloned by limiting dilution. Clone F12-3C8 was selected based upon specificity, and interference criteria.

Horseradish peroxidase conjugate reagent

Horseradish peroxidase (HRP) conjugate reagent was prepared with a hydrazide derivative of xylene using the conventional periodate method (see Nakane et al J. Histochem. Cytochem. 22:1084 (1971)).

Antibody Coated tubes

Antibody coated tubes were prepared by passively coating polystyrene (12×75 mm, NUNC) tubes with the monoclonal F12-3C8 antibody diluted in PBS and incubating overnight.

Example 2

Petroleum Immunoassay Procedure—10 ppm in Soil

The immunoassay method of the present invention has been demonstrated as follows:

10 g of a soil sample were placed in an extraction vial containing 20 mL of methanol and 5 steel pellets (6 mm) and the vial and its contents shaken for 1 minute to disperse the soil particles and extract the petroleum hydrocarbons. The sample was then filtered to clarify the sample using a filter of glass fiber and 0.45μTeflon. 45 uL of the clarified filtrate sample was mixed with 955 μl of 10 mM PBS (pH=7.4) and the resulting mixture added to lyophilized enzyme conjugate reagent (0.3 μg) and mixed. At the same time, 2×45 uL of the xylene standard are similarly treated. The sample and the two standards were then poured into three identical antibody coated tubes, respectively, and the resulting solution mixed. The resulting solution was incubated for 10 minutes at ambient temperature and then washed 4× with a wash buffer (detergent-saline solution). 250 uL of tetramethylbenzidene solution (KP Laboratories, Cat. No. 50-76-02) was added along with 250 uL of hydrogen peroxide solution (KPL, Cat. No. 50-65-02) and the resultant solution mixed. After incubating for 2.5 minutes the color development reaction was stopped with 250 uL of stop solution (1M sulfuric acid).

The optical density (OD) of the test sample was compared to the OD of the xylene standard (6 ppm) which was tested simultaneously with the sample. If the sample OD is less than the standard OD, the sample contains more than 10 ppm gasoline equivalents of refined petroleum products. If the sample OD is greater than the standard OD, the sample contains less than 10 ppm gasoline. Other concentration ranges can be assessed by diluting the test samples with suitable diluents, as long as they are non-reactive with the components of the assay.

The sensitivity of the soil test was established to be 10 ppm for gasoline in soil (see Table I below) with >95% confidence. This detection level was selected on the basis of the limits imposed by UST offices of most state regulatory agencies. To develop the test for detection at this level, the concentration of xylene in the kit standard was set to coincide with the mid-point of the immunoassay dose response curve, the most precise portion of the curve. Also, the antibody concentration immobilized on the tubes and the sample dilution protocol were adjusted so that samples containing 10 ppm or more gasoline were positive (i.e. lower absorbance) versus the absorbance of the kit standard. Table I shows that gasoline spiked into methanol at the soil equivalent concentration of 10 ppm was positive with greater than 95% confidence.

TABLE I

| Gasoline Spiked into Methanol or Extract (ppm) | Percent Negative Results |
|---|---|
| 0 | 92 ± 16% |
| 5 | 51 ± 39% |
| 10 | 0.5 ± 1.4% |

Figure 1:
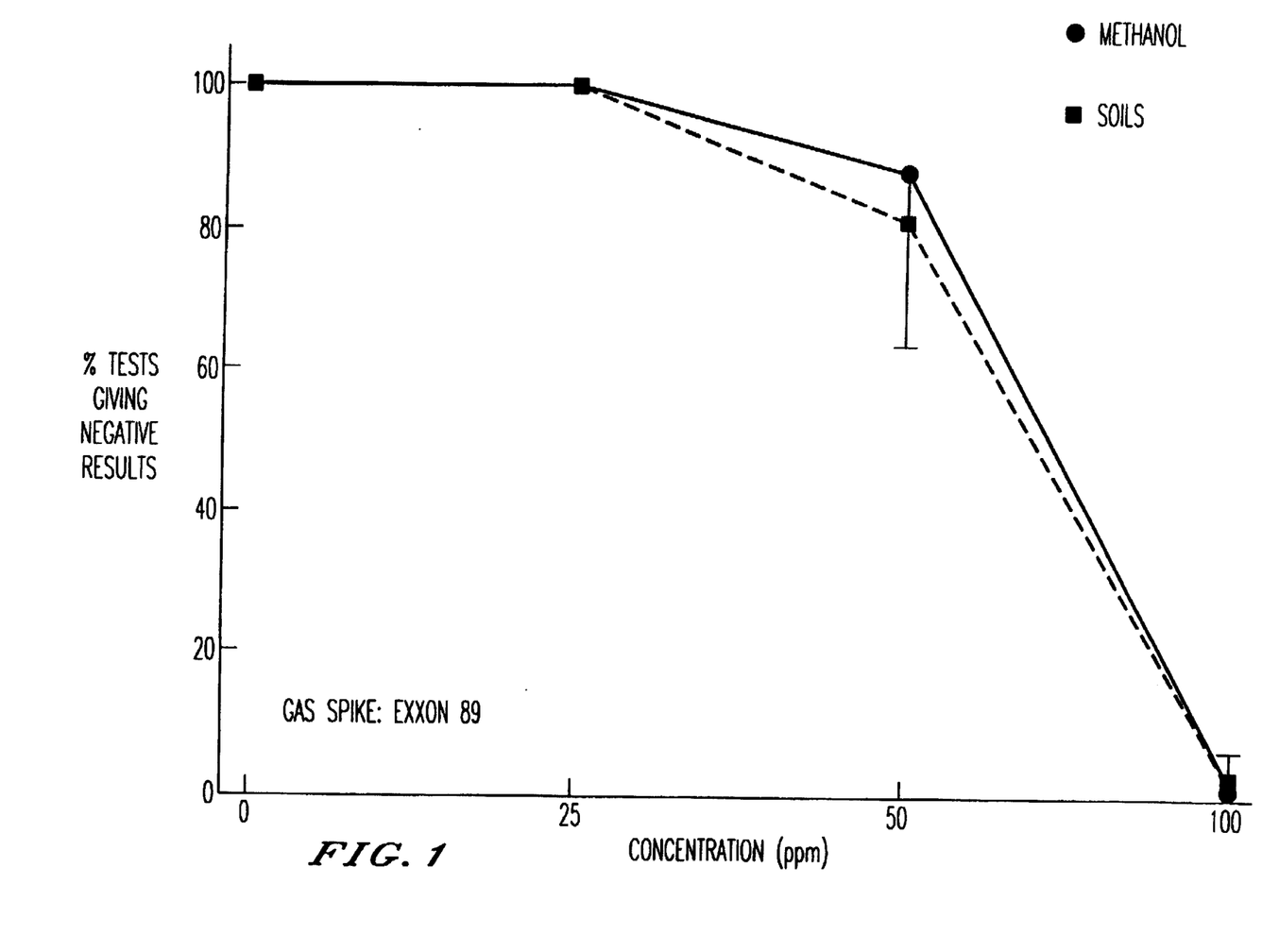
FIG. 1 depicts the sensitivity of the petroleum immunoassay of the present invention to gasoline.

Matrix interference in soils was assessed by determining the assay sensitivity (recovery of spiked samples) in soil extracts confirmed to be negative by GC analysis. Since the sensitivity of the assay was barely changed when spiked negative extracts were compared to spiked methanol samples (FIG. 1), it was concluded that there was negligible soil matrix interference.

Another criterion, in demonstrating the performance of the assay of the present invention, was to determine the sensitivity to other cross-reacting petroleum related compounds. Almost identical sensitivities were found when different brands and octane ratings of gasolines were tested (Table II). Tables III and IV show that there is significant cross-reactivity with petroleum compounds from the semi-volatile and volatile fractions. Greases and oils were not reactive. A selected population of small polyaromatic hydrocarbon compounds (PAH) were detected at low concentrations with the test kit. The fact that the test is so sensitive to PAHs may explain why the sensitivity of the assay for gasoline and diesel are similar, since diesel contains a higher concentration of PAH's and gasoline contains a higher concentration of monocyclic aromatics than diesel. Straight and branched chain alkanes reacted if they were composed of 8 or less carbon atoms. Thus, the test is specific for a defined group of volatile and semi-volatile compounds in petroleum products.

TABLE II

Comparison of gasoline brands with different octane levels, treated at 100 ppm.
Gasoline was spiked into methanol at the indicated soil equivalent concentrations. The assay was performed according to the test protocol.

| Brand | Octane | Number of Replicate Tests | % Test Neg. at 50 ppm | % Test Neg. at 100 ppm |
|---|---|---|---|---|
| CROWN | 87 | 10 | 100 | 0 |
| CROWN | 89 | 10 | 100 | 0 |
| CROWN | 92 | 10 | 90 | 0 |
| BP | 89 | 10 | 90 | 0 |
| BP | 92 | 10 | 100 | 0 |
| MOBIL | 89 | 5 | 100 | 0 |
| TEXACO | 89 | 4 | 100 | 0 |

TABLE III

Cross-reactivity of immunoassay of the present invention (relative to m-xylene = 100% cross reactivity.

Cross-Reactivity of Compounds

| Compound | ED50 (ppb) | % Cross-Reactivity |
|---|---|---|
| m-Xylene | 483 | 100 |
| o-Xylene | 178 | 271 |
| p-Xylene | 1,255 | 38 |
| Ethylbenzene | 176 | 275 |
| Toluene | 2,210 | 22 |
| Benzene | Negative | <1 |
| Acenaphthene | 9 | 5,378 |
| Naphthalene | 11 | 4,390 |
| Phenanthrene | 57 | 848 |
| Methylnaphthalene | 62 | 780 |
| n-Heptane | 1,669 | 30 |
| n-Octane | 4,589 | 11 |
| n-Nonane | Negative | <1 |
| n-Undecane | Negative | <1 |
| n-Tridecane | Negative | <1 |
| n-Tetradecane | Negative | <1 |
| 2-Methylpentane | 851 | 57 |
| 2-Methylhexane | 1,113 | 43 |
| 2,2,4-Trimethylpentane | Negative | <1 |
| Cyclohexane | 6,636 | 7 |
| PCB | Negative | <1 |
| Humic Acid | Negative | <1 |
| Kerosene | 481 | 100 |

The $ED_{50}$ value was calculated from a dose response curve.
Percent Cross-Reactivity = ((m-Xylene $ED_{50}$/Compound $ED_{50}$) × 100).

TABLE IV

Cross-reactivity of the immunoassay of the present invention. The test compounds were dissolved in methanol and assayed. The values listed are the concentration of compound needed to provide a positive result.

| Test Compound | Conc. where positive (ppm) |
|---|---|
| Gasoline (Exxon 89) | 100 |
| Diesel | 75 |
| Kerosene | 100 |
| Jet Fuel | 100 |
| Fuel Oil #2 | 100 |
| Xylene | 100 |
| Toluene | 300 |
| Benzene | >10,000 |
| Grease | >10,000 |
| Brake fluid | >10,000 |
| Naphthalene | 2.5 |
| Acenaphthene | 2.5 |
| Phenanthrene | 10 |
| Me-naphthalene | 10 |
| Hexane | 300 |
| Isooctane | 100 |
| Heptane | 300 |
| Undecane | >10,000 |
| PCB | >10,000 |
| Humic Acid | >10,000 |

Figure 2:
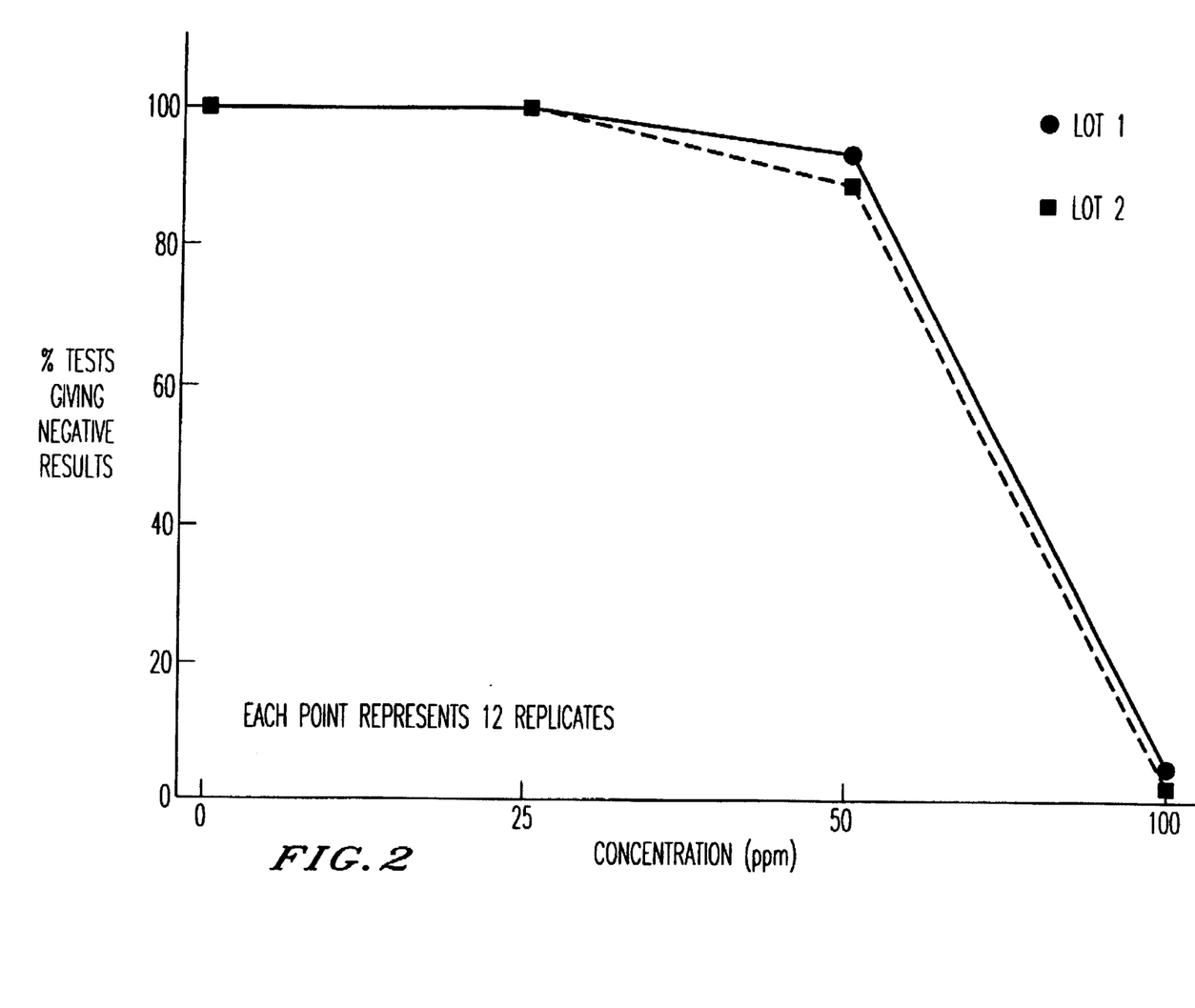
FIG. 2 represents an assessment of variation in the petroleum immunoassay of the present invention.

Example 5. Reproducibility from person-to-person, day-to-day, and lot-to-lot was investigated. The average absorbance produced by the immunoassay in response to the standard was 1.04±0.08 AU (SD) for one operator and 1.05±0.09 AU (SD) for the second operator when 72 repetitions were performed using 6 different soils. This data demonstrates that there is little protocol induced variability between two people performing the assay. The difference between lots was found to be insignificant (FIG. 2). Since the assays to illustrate lot-to-lot and person-to-person variability were performed on different days, there is no significant protocol induced variability from day-to-day. These experiments indicate that the product is reproducible and not subject to inter-person, day or lot variations.

Sensitivity profiles on spiked or negative soil were used to evaluate the effective temperature range. The accuracy, sensitivity and specificity of the test remained constant over the range of 4°–37° C.

Figure 3:
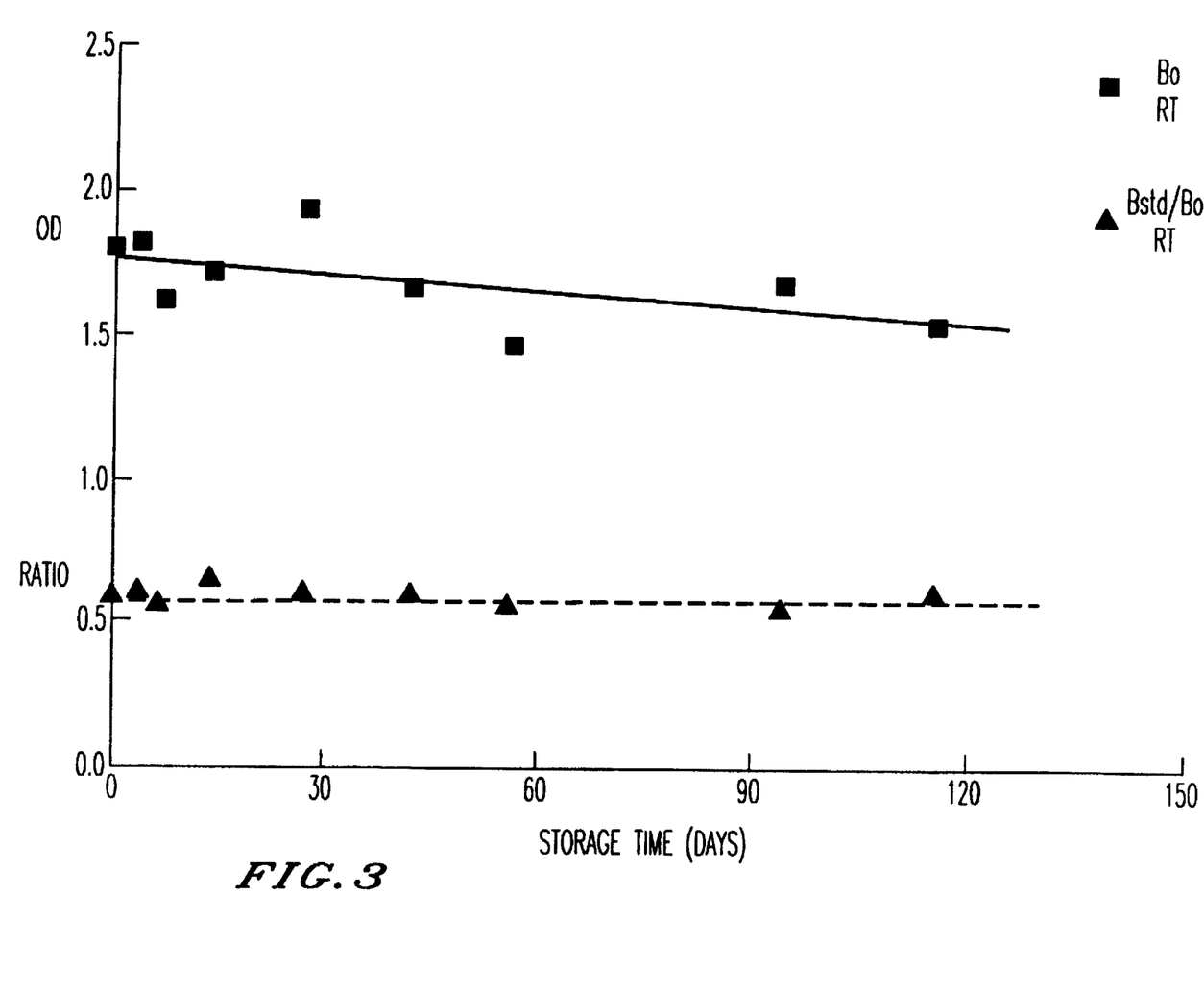
FIG. 3 shows the stability of the kit of the present invention.

Example 6. The assay test kit of the present invention showed little loss in performance when stored at room temperature (20°–30° C.) for 4 months (FIG. 3). Regression analysis evaluating signal decay and performance suggests long-term stability (>6 months) when stored at room temperature.

Example 7. A limited field study demonstrated that the assay test kit of the present invention correlated to the values obtained with IR Method 418.1 and GC Method 801.5 (see Table V). Samples obtained from a railroad site contaminated with diesel fuel were tested with the immunoassay of the present invention and compared to testing of split samples analyzed using the conventional IR and GC methods. The amounts of diesel fuel found by the field tests of the present invention correlated well with the values obtained using the conventional laboratory methods. Additionally, Table VI shows the correlation of the present field method with the conventional IR method in detection of gasoline in soils. Since the samples were contaminated with gasoline, it is not surprising that the immunoassay, in some cases, showed a higher level of contamination. The 418.1 method can "lose"(i.e. not detect) a significant portion of the gasoline fraction (see US EPA 600/4-79-0202, revised Mar. 1983). Therefore, the data suggest that the assay method of the present invention is an acceptable, and more conservative, field screening method for petroleum products.

TABLE V

Soil assay test correlation with conventional IR and GC methods.

| Sample ID | GC extractibles (ppm) | IR | 75 ppm Test Result | Evaluation GC | Evaluation IR | 750 ppm Test Result | Evaluation GC | Evaluation IR |
|---|---|---|---|---|---|---|---|---|
| 1 | 5,720 | 20,800 | ≥75 | ● | ● | ≥750 | ● | ● |
| 2 | 610 | 14,700 | ≥75 | ● | ● | ≥750 | FP | ● |
| 3 | 370 | 6,800 | ≥75 | ● | ● | ≥750 | FP | ● |
| 4 | 2,270 | 1,950 | ≥75 | ● | ● | ≥750 | ● | ● |
| 5 | 4,870 | 18,600 | ≥75 | ● | ● | ≥750 | ● | ● |
| 6 | 760 | 1,180 | ≥75 | ● | ● | <750 | FN* | FN |
| 7 | 66 | 4,100 | ≥75 | FP* | ● | <750 | ● | FN |
| 8 | 303 | 2,100 | ≥75 | ● | ● | <750 | ● | FN |
| 9 | 20,400 | 29,600 | ≥75 | ● | ● | ≥750 | ● | ● |
| 10 | 26,300 | 28,600 | ≥75 | ● | ● | ≥750 | ● | ● |
| 11 | 267 | 330 | ≥75 | ● | ● | ≥750 | FP | FP |
| 12 | 550 | 22,700 | ≥75 | ● | ● | ≥750 | FP | ● |
| 13 | 59,300 | 64,400 | ≥75 | ● | ● | ≥750 | ● | ● |
| 14 | 26,500 | 12,900 | ≥75 | ● | ● | ≥750 | ● | ● |

●-immunoassay and GC or IR results agree
FP-false positive
FN-false negative
FP*-also positive but within 25% of GC or IR results
FN*-also negative but within 25% of GC or IR results

TABLE VI

Field study - Comparison between the immunoassay of the present invention and the reference TRPH (IR) method.

| Samples No. | Present invention ppm | TRPH (IR-418.1) ppm |
|---|---|---|
| ST-01 | <100 | <20 |
| ST-02 | >1000 | 520 |
| ST-03 | >1000 | 1700 |
| ST-04 | 100–1000 | 130 |
| ST-05 | 100–1000 | 20 |
| ST-06 | 100–1000 | 40 |
| ST-07 | 100–1000 | 400 |
| ST-08 | 100–1000 | 640 |
| ST-09 | >1000 | 1600 |

The advantages of immunoassay technology can be attributed to the underlying lock and key binding principle and its compatibility with aqueous matrixes. This method does not require the chromatographic separation of sample components, nor does it require that compounds absorb visible, infrared or UV for detection. Interferences from other compounds are considerably less of a problem because of the conformational nature of the antibody binding process. Sample processing time is significantly reduced, and the direct testing of aqueous samples, or water-compatible leachates of soil, can be performed. The technology offers a unique, and conservative, approach to field screening. The incidence of false negative data is exceptionally low. Aspects that tend to interfere with immunoassay methods of this type tend to cause an overestimation of contamination, or false positive result by minimizing the binding of enzyme conjugate to antibody or suppressing signal generation by the enzyme.

This method offers significant versatility and performance advantages. It is a convenient and effective new tool that can enhance the efficiency of site management activities and the utilization of our national laboratory system.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A monoclonal antibody useful for detecting the presence of petroleum-based fuel in a sample, which specifically binds a characteristic plurality of compounds found in petroleum-based fuel, said characteristic plurality of compounds being a $C_{1-2}$ alkyl substituted monocyclic aromatic hydrocarbon and unsubstituted bi- and tri-cyclic aromatic hydrocarbons, wherein said monoclonal antibody has a cross reactivity with benzene of <1%, wherein said monoclonal antibody is obtained by a process comprising:

(i) producing an immune response in a vertebrate host by immunization with an immunogen comprised of a derivative moiety of the formula.

wherein
$R^1$ to $R^5$ are each independently H, $CH_3$ or $CH_2CH_3$;
X and Y are each, independently or a single bond wherein $R^6$ is selected from the group consisting of H, $C_1$–$C_2$ alkyls, and linear, branched and cyclic $C_3$–$C_6$ alkyls; and n is 0 or an integer from 1 to 4, linked to an immunogen carrier molecule;

(ii) preparing a hybridoma from the lymphoid cells of said host;

(iii) selecting said hybridoma to produce said monoclonal antibody; and

(iv) obtaining said monoclonal antibody.

2. A monoclonal antibody which specifically binds toluene, xylene, ethylbenzene, naphthalene, methylnaphthalene, phenanthrene, and acenaphthene, wherein said monoclonal antibody has a cross reactivity with benzene of <1%, wherein said monoclonal antibody is obtained by a process comprising:

(i) producing an immune response in a vertebrate host by immunization with an immunogen comprised of a derivative moiety of the formula wherein
$R^1$ to $R^5$ are each independently H, $CH_3$ or $CH_2CH_3$;
X and Y are each, independently or a single bond wherein $R^6$ is selected from the group consisting of H, $C_1$–$C_2$ alkyls, and linear, branched and cyclic $C_3$–$C_6$ alkyls; and n is 0 or an integer from 1 to 4, linked to an immunogen carrier molecule;

(ii) preparing a hybridoma from the lymphoid cells of said host;

(iii) selecting said hybridoma to produce said monoclonal antibody; and (iv) obtaining said monoclonal antibody.

3. The monoclonal antibody of claim 2, which further specific for n-heptane, 2-methylhexane, 2-methylpentane and n-octane.

4. An enzyme immunoassay kit useful for detecting the presence of petroleum-based fuel in a sample, comprising a monoclonal antibody which specifically binds toluene, xylene, ethylbenzene, naphthalene, methylnaphthalene, phenanthrene, and acenaphthene, wherein said monoclonal antibody is obtained by a process comprising:

(i) producing an immune response in a vertebrate host by immunization with an immunogen comprised of a derivative moiety of the formula wherein
$R^1$ to $R^5$ are each independently H, $CH_3$ or $CH_2CH_3$;
X and Y are each, independently or a single bond wherein $R^6$ is selected from the group consisting of H, $C_1$–$C_2$ alkyls, and linear, branched and cyclic $C_3$–$C_6$ alkyls; and
n is 0 or an integer from 1 to 4, linked to an immunogen carrier molecule;

(ii) preparing a hybridoma from the lymphoid cells of said host;

(iii) selecting said hybridoma to produce said monoclonal antibody; and (iv) obtaining said monoclonal antibody.

5. A homogeneous enzyme immunoassay kit according to claim 4.

6. The homogeneous enzyme immunoassay kit of claim 5, wherein said enzyme has been lyophilized.

7. An enzyme-linked immunoassay kit according to claim 4.

8. The enzyme-linked immunoassay kit of claim 7, wherein said enzyme has been lyophilized.

9. A monoclonal antibody useful for detecting the presence of petroleum-based fuel in a sample, which specifically binds a characteristic plurality of compounds found in petroleum-based fuel, said characteristic plurality of compounds being a $C_{1-2}$ alkyl substituted monocyclic aromatic hydrocarbon, unsubstituted bi- and tri-cyclic aromatic hydrocarbons and a $C_{6-8}$ aliphatic hydrocarbon selected from the group consisting of n-heptane, 2-methylhexane, 2-methylpentane and n-octane, wherein said monoclonal antibody specifically binds said characteristic plurality of compound to provide substantially equivalent detection of petroleum-based fuels, said petroleum based fuels being gasoline, diesel, kerosene, jet fuel and fuel oil #2 wherein said monoclonal antibody has a cross reactivity with benzene of <1%.

10. An immunoassay for determining the presence of petroleum-based fuel in a sample, comprising:

(i) combining (ia) a monoclonal antibody, as claimed in claim 1, which specifically binds a characteristic plurality of compounds found in petroleum based fuels, with (ib) a mixture of (ibi) the sample and (ibii) a hapten-and-reporter-moiety-containing reagent which is cross reactive with said monoclonal antibody, wherein said reporter moiety is susceptible to producing a detectable signal, to form an assay mixture; said characteristic plurality of compounds being toluene, xylene, ethylbenzene, naphthalene, methylnaphthalene, phenanthrene, and acenaphthene, (2) preparing a hybridoma from the lymphoid cells of said host;

(3) selecting said hybridoma to produce said monoclonal antibody; and

(4) obtaining said monoclonal antibody;

(ii) incubating said assay mixture to allow competitive monoclonal antibody binding between at least one of said characteristic plurality of compounds, if present, in the sample, and said reagent;

(iii) causing production of said signal and correlating said signal to the amount of reagent bound to said monoclonal antibody to obtain a measure of the amount of petroleum-based fuel in said sample.

11. The immunoassay of claim 10, wherein said monoclonal antibody is an immobilized monoclonal antibody.

12. The immunoassay of claim 10, comprising using said reagent of the formula wherein
$R^1$ to $R^5$ are each independently H, $CH_3$ or $CH_2CH_3$;
X and Y are each, independently or a single bond wherein $R^6$ is selected from the group consisting of H, $C_1$–$C_2$ alkyls, and linear, branched and cyclic $C_3$–$C_6$ alkyls; and n is 0 or an integer from 1 to 4.

13. The immunoassay of claim 12, wherein said reporter moiety is an enzyme selected from the group consisting of horseradish peroxidase, alkaline phosphates, and β-galactosidase.

14. The immunoassay of claim 13, wherein said enzyme is horseradish peroxidase.

15. The immunoassay of claim 12, wherein $R_2$ and $R_4$ are —$CH_3$, X is —$CH_2$—CO—NH—, Y is —NH—, n is 2, and said reporter moiety is horseradish peroxidase.

16. The immunoassay of claim 10, further comprising simultaneously assaying a standard solution of at least one of the characteristic plurality of compounds found in petroleum-based fuel and said sample.

* * * * *